United States Patent
Shasho et al.

(10) Patent No.: US 6,573,384 B1
(45) Date of Patent: Jun. 3, 2003

(54) PROCESS FOR PRODUCTION OF INDOLE DERIVATIVES AND INTERMEDIATES THEREFOR

(75) Inventors: Manabu Shasho, Ibaraki (JP); Yuki Komatsu, Ibaraki (JP); Mamoru Miyazawa, Ibaraki (JP); Kimihiro Matsuo, Ibaraki (JP); Susumu Inoue, Ibaraki (JP); Kohshi Ueno, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/937,929
(22) PCT Filed: Apr. 1, 2000
(86) PCT No.: PCT/JP00/02381
§ 371 (c)(1), (2), (4) Date: Nov. 13, 2001
(87) PCT Pub. No.: WO00/61575
PCT Pub. Date: Oct. 19, 2000

(30) Foreign Application Priority Data

Apr. 12, 1999 (JP) ............................................. 11-104084
Mar. 16, 2000 (JP) ....................................... 2000-073283

(51) Int. Cl.[7] .................... C07D 401/04; C07D 211/58
(52) U.S. Cl. ...................................... 546/201; 546/223
(58) Field of Search ................................. 546/201, 223

(56) References Cited

FOREIGN PATENT DOCUMENTS

| EP | A1 0 976 732 | * | 2/2000 |
| WO | A1-9843956 | * | 10/1998 |
| WO | WO 00/23075 | * | 4/2000 |

* cited by examiner

*Primary Examiner*—Ceila Chang
(74) *Attorney, Agent, or Firm*—Birch, Stewart, Kolasch & Birch, LLP

(57) ABSTRACT

To provide a novel, industrially superior process for producing a 1,4-substituted cyclic amine compound which is useful as a pharmaceutical, and an intermediate for the process. That is, a process for producing an indole compound (I), which comprises reducing a 1,4-subsutituted 2-nitrophenyl compound (VII) to give a 1,4-substituted 2-aminophenyl compound (V); reacting the compound (V) with an N-substituted 4-piperidone compound (VI) to give a 1,4-substituted 2-piperidylaminophenyl compound (IV); cyclizing the compound (IV) to give a 2-oxoindoline compound (III); halogenating the compound (III) to give a 2-halogenated indole compound (II); reducing the compound (II); and if necessary subjecting the resulting compound to alcoholysis or aminolysis.

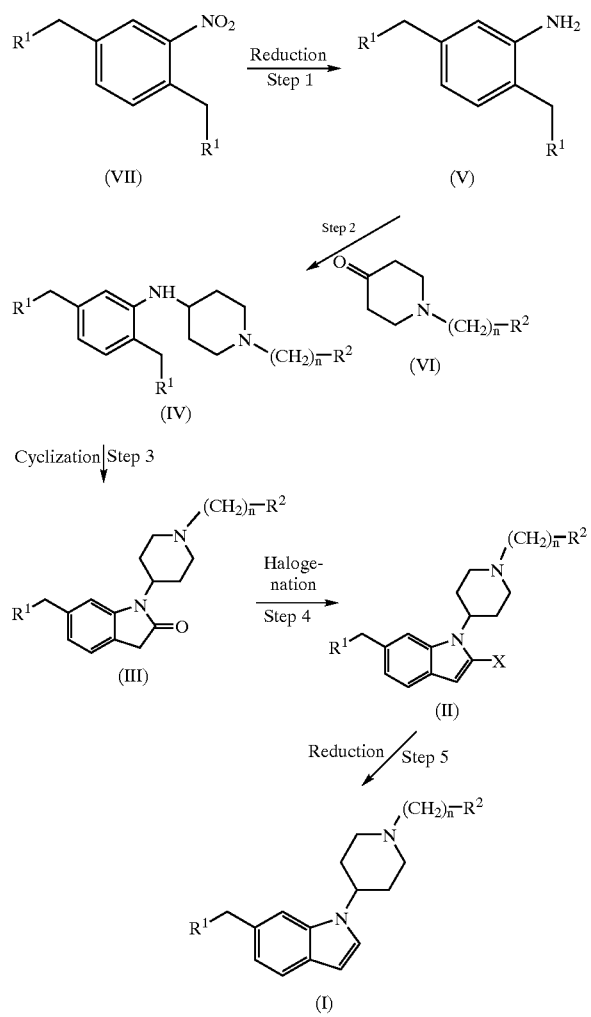

wherein each of $R^1$ and $R^2$ represents a substituent; X represents a halogen atom; and n is a numerical subscript.

15 Claims, No Drawings

PROCESS FOR PRODUCTION OF INDOLE DERIVATIVES AND INTERMEDIATES THEREFOR

This application is the national phase under 35 U.S.C. § 371 of PCT International Application No. PCT/JP00/02381 which has an International filing date of Apr. 12, 2000, which designated the United States of America.

FIELD OF THE INVENTION

The present invention relates to a novel, industrially superior process for the production of 1,4-substituted cyclic amine compound such as those disclosed in WO 98/43956 which are useful as pharmaceuticals and to intermediates thereof.

PRIOR ART

Among the 1,4-substituted cyclic amine compounds disclosed in WO 98/43956, indole compounds which are target compounds of the present invention have been prepared primarily by synthesizing corresponding indoline compounds and then oxidizing the indoline compounds.

This is because the NH group in the indoles has low reactivity and, therefore, it is difficult to directly add a side chain thereto.

In the oxidation of the indoles, various oxidizing agents can be used, and manganese dioxide is frequently used. However, the oxidation using manganese dioxide is rate-limited by stirring because it is a heterogeneous reaction, and therefore a large-volume treatment on an industrial scale is hardly achieved. In addition, since the reactivity of the oxidation depends on the degree of activation of the catalyst, the reaction usually takes several hours to complete, and in some cases, takes one day or longer. Moreover, when manganese dioxide is re-used repeatedly, its activity decreases, and this may have a large effect on production costs.

On the other hand, other oxidizing agents, such as permanganates, hydrogen peroxide, nitric acid, lead tetraacetate, mercuric acetate, potassium nitrosodisulfate (Fremy's salt), 2,3-dichloro-5,6-dicyano-1,4-benzoquinone (DDQ) and tetrachldrobenzoquinone (chloranil) have good reactivity. However, with such oxidizing agents, there have been problems such as the occurrence of adverse side reactions due to their high activities, poor storage properties, toxicity and poor safety, and generally being expensive, and therefore are not always suitable for industrial applications.

In these situations, the present inventors have conducted extensive studies for the purpose of developing a novel production process which is useful from the viewpoints of stability of raw materials, production costs, ease of operation (e.g., workability, safety, non-toxicity), purity of the final product and so on.

As a result, the inventors have found that the process described in detail hereinbelow can solve the above-mentioned problems at a stroke and have accomplished the present invention.

DISCLOSURE OF THE INVENTION

Accordingly, the object of the present invention is to provide a novel process for the production of indole compounds which are useful as fine chemicals such as pharmaceuticals, and to provide intermediates for the process.

Herein, the indole compound (I) according to the present invention is represented by the following formula:

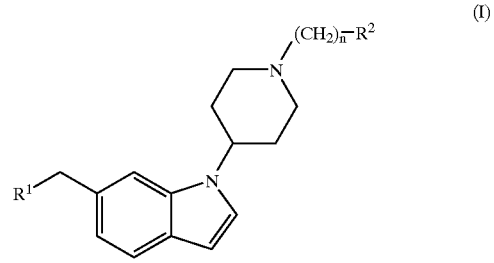

wherein $R^1$ represents hydroxymethyl group, carboxyl group, a lower alkoxycarbonyl group or a carbamoyl group in which the nitrogen atom may be substituted; $R^2$ represents an aryl. group which may be substituted, a heteroaryl group which may be substituted or a benzoheteroaryl group which may be substituted; and n is 0 or an integer from 1 to 6.

In the above definition, the hydroxymethyl group refers to a group represented by the formula —CH$_2$OH, and the carboxyl group refers to a group represented by the formula —COOH.

The lower alkoxycarbonyl group refers to a group represented by the formula —COOR, wherein R represents a linear or branched lower alkyl group having 1 to 6 carbon atoms.

The carbamoyl group which may be substituted refers to a carbamoyl group in which the nitrogen atom may be substituted by a lower alkyl group or the like, wherein the nitrogen atom may be included in a cyclic amine. Specifically, for example, carbamoyl (—CONH$_2$), N-methylcarbamoyl (—CONHCH$_3$), N,N-dimethylcarbamoyl (—CON(CH$_3$)$_2$), N-ethylcarbamoyl (—CONHC$_2$H$_5$), N,N-diethylcarbamoyl (—CON(C$_2$H$_5$)$_2$), N-methyl-N-ethylcarbamoyl (—CON(CH$_3$)C$_2$H$_5$), N-propylcarbamoyl (—CONHC$_3$H$_7$), 1-pyrrolidinylcarbonyl, 1-pyrazolynylcarbonyl, 1-piperidylcarbonyl, 1-piperazinylcarbonyl, 4-morpholinylcarbonyl and 4-thiomorpholinylcarbonyl groups. Among these, N-methylcarbamoyl, N-ethylcarbamoyl or N-propylcarbamoyl group is preferred from the viewpoints of pharmacological activity and safety.

The aryl group which may be substituted refers to a group derived from an aromatic ring such as a phenyl or naphthyl group, which may not be substituted or have a substituent. Examples of the substituent include the following members.

(1) halogen atom;
(2) hydroxyl group;
(3) a lower alkyl group;
(4) a lower alkoxy group;
(5) a lower alkoxyalkoxy group;
(6) an amino group in which the nitrogen atom may be substituted;
(7) nitro group;
(8) cyano group;
(9) formyl group;
(10) a lower acyl group;
(11) an aromatic acyl group;
(12) a heteroarylcarbonyl group;
(13) a halogenated lower alkyl group;
(14) a lower alkoxyalkoxy group;
(15) a hydroxy(lower)alkyl group;
(16) a hydroxy(lower)alkoxy group;
(17) a lower alkoxycarbonyl group;
(18) a carbamoyl group in which the nitrogen atom may be substituted;
(19) a lower alkylsulfonyl group;

(20) a lower alkylsulfinyl group;
(21) a sulfamoyl group in which the nitrogen atom may be substituted;
(22) a lower acylamino group;
(23) a lower alkoxycarbonylamino group;
(24) a lower alkylsulfonylamino group;
(25) an arylsulfonylamino group in which the nitrogen atom may be substituted;
(26) a lower alkylsulfonyloxy group;
(27) an alkylenedioxy group;
(28) an aralkyl group;
(29) an aralkyloxy group; and
(30) a tri(lower)alkylsilyl group.

Among these, a halogen atom is more preferred. Specific examples of the halogen atom include fluorine, chlorine, bromine and iodine atoms. Chlorine or fluorine atom is more preferable with regards to pharmacological activity and safety.

The heteroaryl group which may be substituted refers to a group which is derived from a hateroaromatic ring and it may not be substituted or have a substituent. Specific examples thereof include furyl, thienyl, pyrrolyl, imidazolyl, triazolyl, tetrazolyl, oxazolyl, thiazolyl, pyridyl, pyrazinyl and pyrimidinyl groups. The substituent includes those described for the aryl group which may be substituted.

The benzoheteroaryl group which may be substituted refers to a group which is derived from a benzoheteroaromatic ring and may not be substituted or have a substitutent. Specific examples thereof include indolyl, benzothiazolyl, benzoimidazolyl, quinolyl, isoquinolyl, phthaladinyl, quinoxanyl and quinazolynyl groups. The substituent includes those described for the aryl group which may be substituted.

Herein, more specifically as the indole compound (I) according to the present invention, the following compounds may be proposed, but is not limited thereto.
(1) 1-[1-(2-Fluorophenethyl)piperidin-4-yl]-6-methylcarbamoylmethyl indole;
(2) 1-[1-(2-fluorophenethyl)piperidin-4-yl]-6-(N,N-dimethylcarbamoyl)methyl indole;
(3) 1-[1-(4-fluorophenethyl)piperidin-4-yl]-6-methylcarbamoylmethyl indole;
(4) 1-[1-(4-fluorophenethyl)piperidin-4-yl]-6-ethylcarbamoylmethyl indole; and
(5) 1-[1-(4-fluorophenethyl)piperidin-4-yl]-6-(1-piperidinylcarbonyl)methyl indole.

Sequentially, the 2-halogenated indole compound (II) according to the present invention is represented by the following formula:

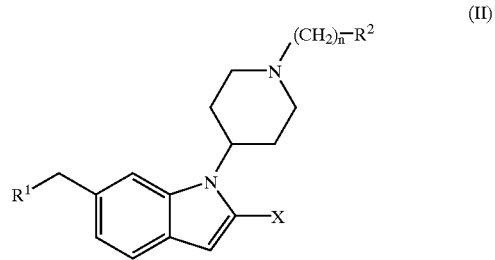

(II)

wherein X represents a halogen atom; and $R^1$, $R^2$ and n have the same meanings as defined above.

The 2-halogenated indole compound (II) is a novel compound and is useful as an intermediate in the novel process for the production of the indole compound (I) of the present invention.

More specifically as the 2-halogenated indole compound (II), the following compounds may be proposed, but is not limited thereto:

(1) ethyl [1-[1-(2-fluorophenethyl)piperidin-4-yl]-2-chloroindol-6-yl]acetate;
(2) ethyl [1-[1-(2-fluorophenethyl)piperidin-4-yl]-2-bromoindol-6-yl]acetate;
(3) ethyl [1-[1-(3-fluorophenethyl)piperidin-4-yl]-2-chloroindol-6-yl]acetate;
(4) ethyl [1-[1-(3-fluorophenethyl)piperidin-4-yl]-2-bromoindol-6-yl]acetate;
(5) ethyl [1-[1-(4-fluorophenethyl)piperidin-4-yl]-2-chloroindol-6-yl]acetate;
(6) ethyl [1-[1-(4-fluorophenethyl)piperidin-4-yl]-2-bromoindol-6-yl]acetate;
(7) ethyl [1-[1-(2-chlorophenethyl)piperidin-4-yl]-2-chloroindol-6-yl]acetate;
(8) ethyl [1-[1-(2-chlorophenethyl)piperidin-4-yl]-2-bromoindol-6-yl]acetate;
(9) ethyl [1-[1-(3-chlorophenethyl)piperidin-4-yl]-2-chloroindol-6-yl]acetate;
(10) ethyl [1-[1-(3-chlorophenethyl)piperidin-4-yl]-2-bromoindol-6-yl]acetate;
(11) ethyl [1-[1-(4-chlorophenethyl)piperidin-4-yl]-2-chloroindol-6-yl]acetate; and
(12) ethyl [1-[1-(4-chlorophenethyl)piperidin-4-yl]-2-bromoindol-6-yl]acetate.

Further, the 2-oxoindoline compound (III) according to the present invention is represented by the following formula:

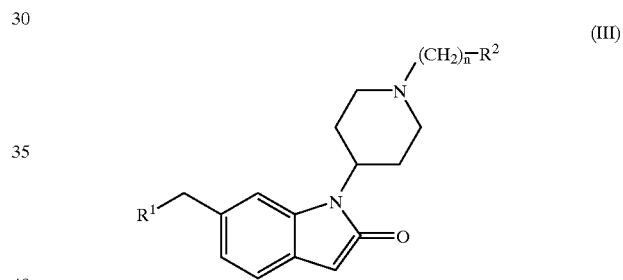

(III)

wherein $R^1$, $R^2$ and n have the same meanings as defined above.

The 2-oxoindoline derivative (III) is a novel compound and is useful as an intermediate in the novel process for the production of the indole derivative (I) of the present invention.

More specifically as the 2-oxoindoline compound (III), the following compounds may be proposed, but is not limited thereto:

(1) ethyl [1-[1-(2-fluorophenethyl)piperidin-4-yl]-2-oxoindolin-6-yl]acetate;
(2) ethyl [1-[1-(3-fluorophenethyl)piperidin-4-yl]-2-oxoindolin-6-yl]acetate;
(3) ethyl [1-[1-(4-fluorophenethyl)piperidin-4-yl]-2-oxoindolin-6-yl]acetate;
(4) ethyl [1-[1-(2-chlorophenethyl)piperidin-4-yl]-2-oxoindolin-6-yl]acetate;
(5) ethyl [1-[1-(3-chlorophenethyl)piperidin-4-yl]-2-oxoindolin-6-yl]acetate; and
(6) ethyl [1-[1-(4-chlorophenethyl)piperidin-4-yl]-2-oxoindolin-6-yl]acetate.

Further, the 1,4-substituted 2-piperidylaminophenyl compound (IV) according to the present invention is represented by the following formula:

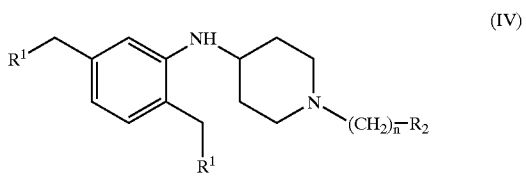 (IV)

wherein $R^1$, $R^2$ and n have the same meanings as defined above.

The 1,4-substituted 2-piperidylaminophenyl compound (IV) is a novel compound and is useful as an intermediate in the novel process for the production of the indole compound (I) of the present invention.

More specifically as the 1,4-substituted 2-piperidylaminophenyl compound (IV), the following compounds may be proposed, but is not limited thereto:

(1) ethyl 2-[1-(2-fluorophenethyl)piperidin-4-yl]aminobenzene-1,4-diacetate;

(2) methyl 2-[1-(3-fluorophenethyl)piperidin-4-yl]aminobenzene-1,4-diacetate;

(3) propyl 2-[1-(4-fluorophenethyl)piperidin-4-yl]aminobenzene-1,4-diacetate;

(4) ethyl 2-[1-(2-chlorophenethyl)piperidin-4-yl]aminobenzene-1,4-diacetate;

(5) methyl 2-[1-(3-chlorophenethyl)piperidin-4-yl]aminobenzene-1,4-diacetate; and (6) propyl 2-[1-(4-chlorophenethyl)piperidin-4-yl]aminobenzene-1,4-diacetate.

Further, the 1,4-substituted 2-aminophenyl compound (V) according to the present invention is represented by the following formula:

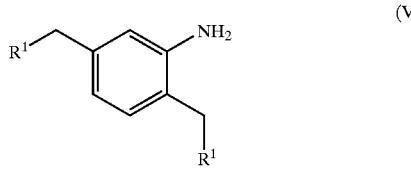 (V)

wherein $R^1$ has the same meaning as defined above.

Further, the N-substituted 4-piperidone compound (VI) according to the present invention is represented by the following formula:

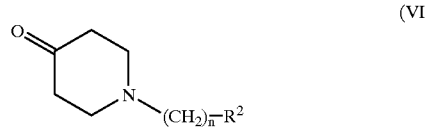 (VI)

wherein $R^2$ and n have the same meanings as defined above.

Finally, the 1,4-substituted 2-nitrophenyl compound (VII) according to the present invention is represented by the following formula:

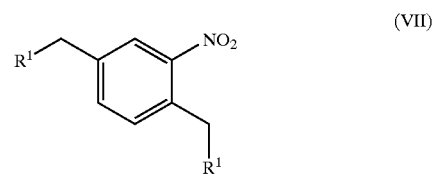 (VII)

wherein $R^1$ has the same meaning as defined above.

Sequentially, the scheme of chemical reactions in the novel process for the production of an indole compound (I) according to the present invention is as follows.

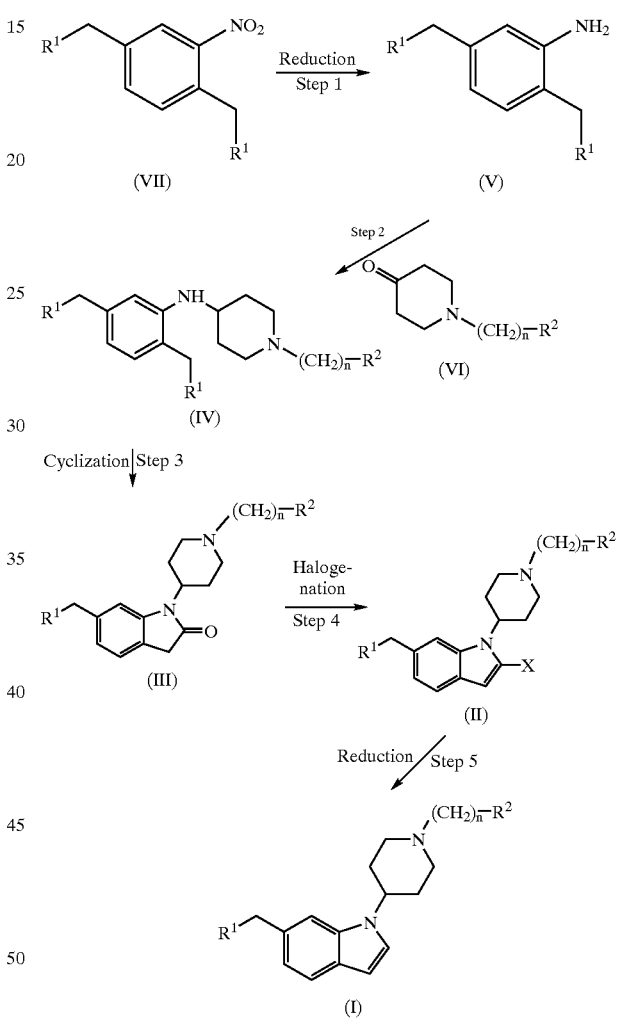

wherein $R^1$, $R^2$, X and n have the same meanings as defined above.

The production process is described in detail below with reference to the above scheme.

(1) Step 1

This step is for reducing a 1,4-substituted 2-nitrophenyl compound (VII), to give a 1,4-substituted 2-aminophenyl compound (V).

The reaction is not particularly limited and any conventional method for the reduction of a nitro group may be employed. However, a contact reduction method is preferred, since the reaction can be achieved efficiently with a high yield.

(2) Step 2

This step is for reductive amidation of the 1,4-substituted 2-aminophenyl compound (V) with a N-substituted 4-piperidone compound (VI), to give a 1,4-substituted 2-piperidylaminophenyl compound (IV).

The reaction may be performed, for example, in accordance with a method as described in the New Experimental Chemical Studies ("Shin Jikken Kagaku Koza") 14-III, p.1380, published by Maruzen.

The reduction method or reducing agent to be used in the reaction is not particularly limited. For example, borane, lithium aluminum hydride, sodium bis(2-methoxyethoxy) aluminum hydride, sodium triacetoxyborohydride, sodium cyanoborohydride and sodium borohydride can be used as the reducing agent.

The reaction can proceed more rapidly and with good selectivity in the presence of boron trifluoride/diethyl ether complex or a Lewis acid (e.g., titanium tetrachloride).

(3) Step 3

This step is for cyclizing the 1,4-substituted 2-piperidylaminophenyl compound (IV), to give a 2-oxoindoline compound (III).

The reaction may be performed by a conventional method under an acidic condition, for example in the presence of sulfuric acid, polyphospholic acid, hydrochloric acid, p-toluenesulfonic acid monohydrate or the like.

(4) Step 4

This step is for halogenating the 2-oxoindoline compound (III), to give a 2-haloganated indole compound (II).

The reaction may be performed using a conventional halogenating agent used for organic synthesis. Specific examples of the halogenating agent include phosphoryl chloride (phosphorous oxychloride), thionyl chloride, sulfuryl chloride, phosphorous trichloride, phosphorous pentachloride, oxalyl chloride, thionyl bromide and phosphorous tribromide.

(5) Step 5

This step is for reducing the 2-haloganated indole compound (II), to give an objective indole compound (I).

As in the case of Step (1), any conventional method for reducing a halogen atom may be employed in the reaction, but a contact reduction method is preferred because the reaction can be achieved effectively and with a good yield.

The objective indole compound (I) may be purified by a conventional method such as column chromatography. The compound may also be purified by crystallization. In this case, the solvent for the crystallization is not particularly limited and any conventional solvent may be used. In particular, a solvent selected from the group consisting of heptane, ethanol, isopropyl acetate, n-propanol and isopropanol, or a mixture thereof may be used to give the compound in a good yield and at a high purity. In this case, examples of the mixed solvent include heptane/ethanol, heptane/isopropyl acetate, heptane/n-propanol and heptane/isopropanol.

EXAMPLES

To illustrate the present invention in more detail, and in no way limit, the following Examples are given.

Example 1

Synthesis of 1-[1-(2-Fluorophenetyl)piperidin-4-yl]-6-methylcarbamoylmethyl Indole 1-1) Ethyl 2-nitrobenzene-1,4-diacetate

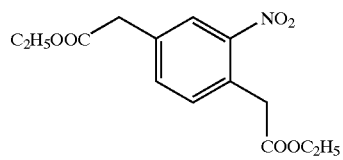

A solution of ethyl benzene-1,4-diacetate (CAS Reg. No. 36076-26-3) (14.0 g; 55.937 mmol) prepared in accordance with JP-A 57-183740 in conc. sulfuric acid (28 ml) was cooled with ethanol/dry ice, and 90% nitric acid (4.0 g; 57.134 mmol) was added dropwise thereto at −5 to 10° C. After 10 min., the reaction solution was added dropwise to a solution of ethyl acetate (140 ml) in ice-water (140 ml). Then, the organic layer was separated and washed with water, a saturated aqueous sodium bicarbonate and brine, followed by adding anhydrous magnesium sulfate and activated charcoal thereto. After filtering, the solvent was removed, to give the title compound (yield: 16.16 g, 54.726 mmol, 97.8%).

m.p.: 50–51° C.; $^1$H-NMR(400 MHz, CDCl$_3$) δ (ppm); 1.27 (3H, t, J=7.1 Hz) 1.28 (3H, t, J=7.1 Hz), 3.70 (2H, s), 4.00 (2H, s), 4.17 (2H, q, J=7.1 Hz), 4.18 (2H, q, J=7.1 Hz), 7.32 (1H,d, J=7.9 Hz), 7.53 (1H, dd, J=7.9, 1.5 Hz), 8.05 (1H, d, J=1.5 Hz).

1–2) Ethyl 2-Aminobenzene-1,4-diacetate

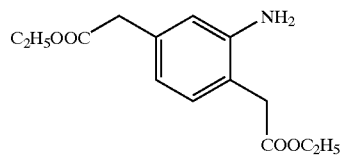

To a solution of ethyl 2-nitrobenzene-1,4-diacetate (16.16 g, 54.726 mmol) in ethyl acetate (100 ml) was added with 10% palladium-carbon (50%) (1.6 g) under ice-cooling. After the reaction system was purged with hydrogen (under atmospheric pressure), the ice bath was removed and the reaction solution was hydrogenated for 4 hours. To the reaction solution was added anhydrous magnesium sulfate to the reaction mixture. After filtering, the solvent was removed, to give the title compound (yield: 14.32 g, 53.977 mmol, 98.6%).

m.p.; 46–47° C.; $^1$H-NMR(400 MHz, CDCl$_3$) δ (ppm); 1.25 (6H, t, J=7.1 Hz), 3.50 (2H, s), 3.52 (2H, s), 4.13 (2H, q, J=7.1 Hz), 4.14 (2H, q, J=7.1 Hz), 4.25 (2H, bs), 6.65 (1H, d, J=1.5 Hz), 6.66 (1H, dd, J=8.2, 1.5 Hz), 7.03 (1H, d, J=8.2 Hz).

1-3) Ethyl 2-[1-(2-Fluorophenetyl)piperidin-4-yl]aminobenzene-1,4-diacetate

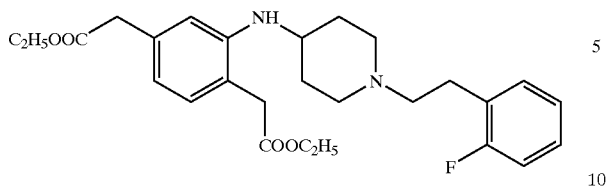

1-(2-Fluorophenetyl)piperidin-4-one (9.34 g, 42.211 mmol) prepared in accordance with Example 348-1) of WO 98/43956 and boron trifluoride/diethyl ether complex (5.5 ml, 43.402 mmol) were added to a solution of ethyl 2-aminobenzene-1,4-diacetate (10.0 g, 37.693 mmol) in ethyl acetate (100 ml) at room temperature. After stirring for 20 min., sodium triacetoxyborohydride (95%) (10.3 g, 46.169 mmol) was added thereto, followed by stirring overnight. The reaction solution was washed with a 2N aqueous sodium hydroxide solution, water and brine, and then added with anhydrous magnesium sulfate and activated charcoal. After filtering, the solvent was removed, to give the title compound as an oil (18.7 g, quantitative).

$^1$H-NMR(400 MHz, CDCl$_3$) δ (ppm); 1.22–1.28 (6H, m), 1.54–1.68 (2H, m), 2.04–2.12 (2H, m), 2.30 (2H, bt, J=9.9 Hz), 2.59–2.65 (2H, m), 2.82–2.89 (2H, m), 2.89–2.97 (2H, m), 3.40 (1H, bs); 3.48 (2H, s), 3.53 (2H, s), 4.08–4.17 (4H, m), 4.46–4.54 (1H, m), 6.59 (1H, s), 6.98–7.09 (3H, m), 7.15–7.26 (3H, m).

1-4) Ethyl [1-[1-(2-Fluorophenetyl)piperidin-4-yl]-2-oxoindolin-6-yl]acetate

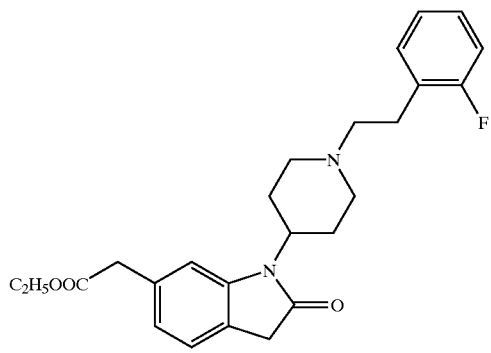

Conc. sulfuric acid (7.6 g, 73.613 mmol) was added dropwise to a solution of ethyl 2-[1-(2-fluorophenetyl)piperidin-4-yl]aminobenzene-1,4-diacetate (15.8 g, 33.576 mmol) in ethanol (160 ml) at room temperature, followed by stirring overnight (to precipitate crystals). After removing ethanol, ethyl acetate was added thereto. The resulting solution was washed with a 2N aqueous sodium hydroxide solution, water and brine, and then added with anhydrous magnesium sulfate and activated charcoal. After filtering, the solvent was removed, to give the title compound (yield: 14.08 g, 168 mmol, 98.8%).

m.p.; 119–120° C.; $^1$H-NMR(400 MHz, CDCl$_3$) δ (ppm); 1.28 (3H, t, J=7.1 Hz), 1.69–1.75 (2H, m), 2.23 (2H, td, J=12.0,2.2 Hz), 2.43–2.54 (2H, m), 2.62–2.68 (2H, m), 2.85–2.91 (2H, m), 3.15 (2H, bd, J=12.0 Hz), 3.49 (2H, s), 3.63 (2H, s), 4.17 (2H, q, J=7.1 Hz), 4.29–4.39 (1H, m), 6.93 (1H, dd, J=7.5, 1.3 Hz), 7.02 (1H, ddd, J=10.0,8.2, 1.3 Hz), 7.07 (1H, dd, J=7.5, 1.3 Hz), 7.09 (1H, d, J=1.3 Hz), 7.16–7.26 (3H, m).

1-5) Ethyl [1-[1-(2-Fluorophenetyl)piperidin-4-yl]-2-chloroindol-6-yl]acetate

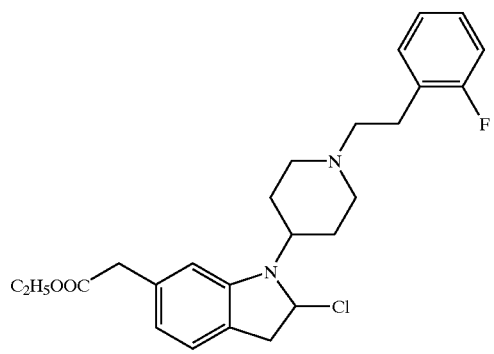

A suspension of ethyl [1-[1-(2-fluorophenetyl)piperidin-4-yl]-2-oxoindolin-6-yl]acetate (32.5 g, 76.559 mmol) in phosphoryl chloride (75.0 ml) was refluxed under heating for 2.5 hours (after 30 min., the suspension was dissolved). After removing the solvent, ethyl acetate (100 ml) and a 2N aqueous sodium hydroxide solution were added thereto, to separate the organic layer. It was washed with a 2N aqueous sodium hydroxide solution, water and brine, and then added with anhydrous magnesium sulfate and activated clay. After filtering, the solvent was removed, to give the title compound (yield: 33.2 g, 74.952 mmol, 97.9%).

m.p.; 82–83° C.; $^1$H-NMR(400 MHz, CDCl$_3$) (ppm); 1.26 (3H, t, J=7.1 Hz), 1.82–1.89 (2H, m), 2.27 (2H, td, J=11.8, 2.1 Hz), 2.62–2.74 (4H, m), 2.88–2.94 (2H, m), 3.21 (2H, d, J=11.8 Hz), 3.71 (2H, s), 4.16 (2H, q, J=7.1 Hz), 4.42–4.51 (1H, m), 6.41 (1H, s), 7.05–7.07 (2H, m), 7.10 (1H, dd, J=7.5, 1.3 Hz), 7.17–7.27 (2H, m), 7.45 (1H, d, J=8.2 Hz), 7.50 (1H, bs).

1-6) [1-[1-(2-Fluorophenetyl)piperidin-4-yl]-6-methylcarbamoylmethyl Indole

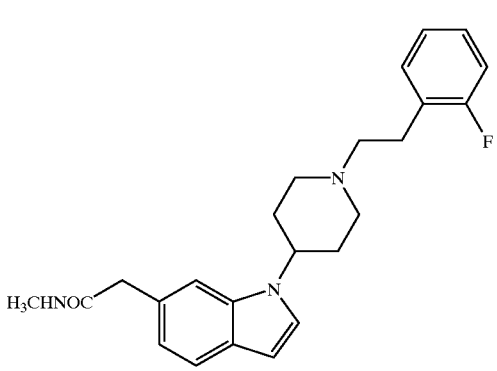

To a solution of ethyl [1-[1-(2-fluorophenetyl)piperidin-4-yl]-2-chloroindol-6-yl]acetate (33.0 g, 74.501 mmol) in methanol (330 ml) was added 10% palladium-carbon (50%) (3.3 g), followed by hydrogenating for 5 hours (under atmospheric pressure). After filtering the reaction solution through Celite, the solvent was removed. The resulting solid was dissolved in a 40% methyl amine/methanol solution (330 ml), followed by stirring at. room temperature overnight. After removing methanol, ethyl acetate was added thereto. It was washed with a 2N aqueous sodium hydroxide solution, water and brine, and then added with anhydrous magnesium sulfate and activated clay. After filtering, the solvent was removed and the resulting residue was re-crystallized from isopropyl acetate, to give the title compound (yield: 20.36 g, 51.741 mmol, 76.7%).

m.p.; 146–147° C.; $^1$H-NMR(400 MHz, CDCl$_3$) δ (ppm); 2.07–2.13 (4H, m), 2.25–2.37 (2H, m), 2.66–2.72 (2H, m), 2.73 (3H, d, J=4.8 Hz), 2.87–2.92 (2H, m), 3.20 (2H, bd, J=12.5 Hz), 3.72 (2H, s), 4.20–4.29 (1H, m), 5.41 (1H, bd, J=4.6 Hz), 6.52 (1H, d, J=3.1 Hz), 6.96 (1H, dd, J=8.1, 1.5 Hz), 7.00–7.06 (1H, m), 7.06–7.10 (1H, m), 7.17–7.28 (4H, m), 7.61 (1H, d, J=8.1 Hz).

What is claimed is:

1. A process for producing an indole compound (I) represented by the following formula:

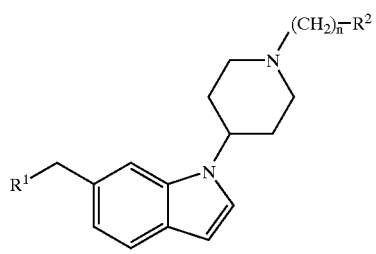

(wherein R$^1$, R$^2$ and n have the same meanings as defined below), which comprises reducing a 2-halogenated indole compound (II) represented by the following formula:

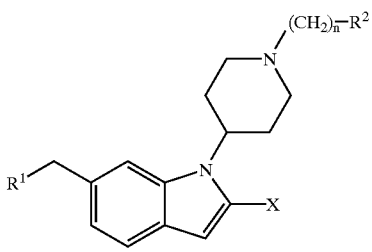

(wherein R$^1$ represents hydroxymethyl group, carboxyl group, a lower alkoxycarbonyl group or a carbamoyl group in which the nitrogen atom may be substituted; R$^2$ represents an aryl group which may be substituted, a heteroaryl group which may be substituted or a benzoheteroaryl group which may be substituted; X represents a halogen atom; and n is 0 or an integer from 1 to 6); and if necessary, subjecting the resulting compound to alcoholysis or aminolysis.

2. A process for producing an indole compound (I), which comprises halogenating a 2-oxoindoline compound (III) represented by the following formula:

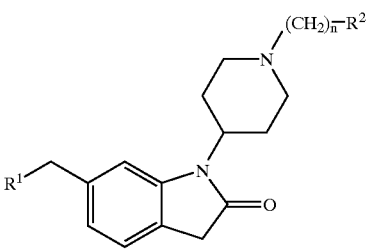

(wherein R$^1$, R$^2$ and n have the same meanings as defined above), to give a 2-haloganated indole compound (II); reducing the compound (II); and if necessary, subjecting the resulting compound to alcoholysis or aminolysis.

3. A process for producing an indole compound (I), which comprises cyclizing a 1,4-substituted 2-piperidylaminophenyl compound (IV) represented by the following formula:

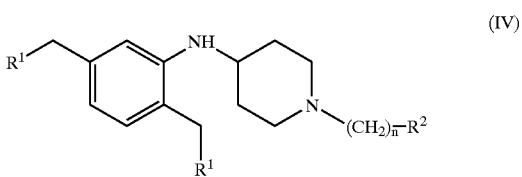

(wherein R$^1$, R$^2$ and n have the same meanings as defined above), to give a 2-oxoindoline compound (III); halogenating the compound (III), to give a 2-halogenated indole compound (II); reducing the compound (II); and if necessary, subjecting the resulting compound to alcoholysis or aminolysis.

4. A process for producing an indole compound (I), which comprises reacting a 1,4-substituted 2-aminophenyl compound (V) represented by the following formula:

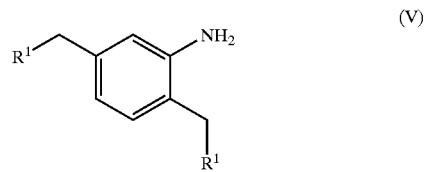

(wherein R$^1$ has the same meaning as defined above) with an N-substituted 4-piperidone compound (VI) represented by the following formula:

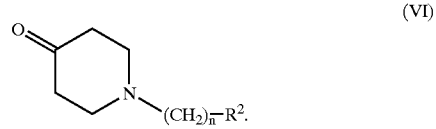

(wherein R$^2$ and n have the same meanings as defined above), to give a 1,4-substituted 2-piperidylaminophenyl compound (IV); cyclizing the compound (IV), to give a 2-oxoindoline compound (III); halogenating the compound (III), to give a 2-haloganated indole compound (II); reducing the compound (II); and if necessary, subjecting the resulting compound to alcoholysis or aminolysis.

5. A process for producing an indole compound (I), which comprises reducing a 1,4-substituted 2-nitrophenyl compound (VII) represented by the following formula:

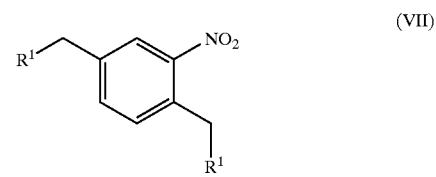

(wherein R$^1$ has the same meaning as defined above), to give a 1,4-substituted 2-aminophenyl compound (V); reacting the compound (V) with an N-substituted 4-piperidone compound (VI), to give a 1,4-substituted piperidylaminophenyl compound (IV); cyclizing the compound (IV), to give a 2-oxoindoline compound (III); halogenating the compound (III), to give a 2-haloganated indole compound (II); reducing the compound (II); and if necessary, subjecting the resulting. compound to alcoholysis or aminolysis.

6. The process according to any of claims 1 to 5, wherein $R^1$ is carbamoyl group in which the nitrogen atom may be substituted.

7. The process according to any of claims 1 to 5, wherein $R^1$ is carbamoyl, an N-(lower)alkylcarbamoyl, an N,N-di(lower)alkylcarbamoyl or an N,N-alkylenecarbamoyl group.

8. The process according to any of claims 1 to 5, wherein $R^2$ is an aryl group which may be substituted.

9. The process according to any of claims 1 to 5, wherein $R^2$ is phenyl group or .a phenyl group having at least one of the same or different substituents selected from the group consisting of the following groups:
(1) halogen atom;
(2) hydroxyl group;
(3) a lower alkyl group;
(4) a lower alkoxy group;
(5) a lower alkoxyalkoxy group;
(6) an amino group in which the nitrogen atom may be substituted;
(7) nitro group;
(8) cyano group;
(9) formyl group;
(10) a lower acyl group;
(11) an aromatic acyl group;
(12) a heteroarylcarbonyl group;
(13) a halogenated lower alkyl group;
(14) a lower alkoxyalkoxy group;
(15) a hydroxy(lower)alkyl group;
(16) a hydroxy(lower)alkoxy group;
(17) a lower alkoxycarbonyl group;
(18) a carbamoyl group in which the nitrogen atom may be substituted;
(19) a lower alkylsulfonyl group;
(20) a lower alkylsulfinyl group;
(21) a sulfamoyl group in which the nitrogen atom may be substituted;
(22) a lower acylamino group;
(23) a lower alkoxycarbonylamino group;.
(24) a lower alkylsulfonylamino group;
(25) an arylsulfonylamino group in which the nitrogen atom may be substituted;
(26) a lower alkylsulfonyloxy group;
(27) an alkylenedioxy group;
(28) an aralkyl group;
(29) an aralkyloxy group; and
(30) a tri(lower)alkylsilyl group.

10. The process according to any of claims 1 to 5, wherein $R^1$ is an N-(lower)alkylcarbamoyl group, $R^2$ is a halogenated phenyl group and n is 0 or an integer from 1 to 3.

11. The process according to any of claims 1 to 5, wherein $R^1$ is N-methylcarbamoyl, N-ethylcarbamoyl or N-propylcarbamoyl group; $R^2$ is chlorophenyl or fluorophenyl group; and n is an integer from 1 to 3.

12. The 2-halogenated indole compound (II) as recited in claim 1.

13. The 2-oxoindoline compound (III) as recited in claim 2.

14. The 1,4-substituted 2-piperidylaminophenyl compound (IV) as recited in claim 3.

15. A process for the crystallization of the indole compound (I) as recited in claim 1, from a solvent selected from the group consisting of heptane, ethanol, isopropyl acetate, n-propanol and iso-propanol, or a mixed solvent of two or more thereof.

* * * * *

UNITED STATES PATENT AND TRADEMARK OFFICE
CERTIFICATE OF CORRECTION

PATENT NO.     : 6,573,384 B1
DATED          : June 3, 2003
INVENTOR(S)    : Shasho et al.

It is certified that error appears in the above-identified patent and that said Letters Patent is hereby corrected as shown below:

<u>Title page,</u>
Item [22], "[22] PCT Filed:    April 1, 2000" change to
-- [22] PCT Filed:    April 12, 2000 --.

Signed and Sealed this

Second Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,573,384 B1
DATED : June 3, 2003
INVENTOR(S) : Sasho et al.

It is certified that error appears in the above-identified patent and that said Letters Patent is hereby corrected as shown below:

Title page,
Item [12], "Shasho et al." should read -- Sasho et al. --
Item [75], Inventors, "Manabu Shasho" should read -- Manabu Sasho --

Column 4,
Formula III, lines 29-40 has a single bond instead of the double bond in one of the rings and should read:

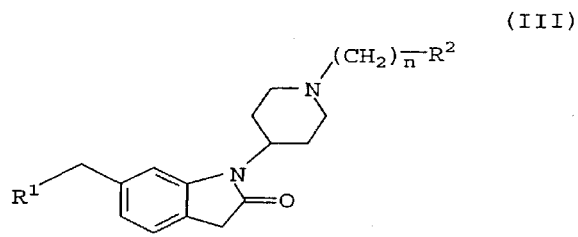

Column 10,
Lines 3-18, has a double bond instead of a single bond in one of the rings and should read:

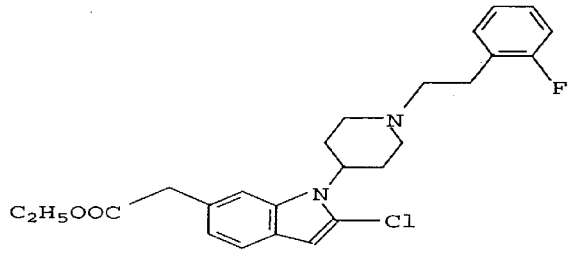

Signed and Sealed this

Twenty-seventh Day of July, 2004

JON W. DUDAS
*Acting Director of the United States Patent and Trademark Office*